United States Patent
O'Neill

(10) Patent No.: US 8,012,163 B2
(45) Date of Patent: Sep. 6, 2011

(54) OCCLUDING AND STABILIZING MEDICAL DEVICE

(75) Inventor: William G. O'Neill, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1364 days.

(21) Appl. No.: 10/078,303

(22) Filed: Feb. 15, 2002

(65) Prior Publication Data

US 2003/0158461 A1    Aug. 21, 2003

(51) Int. Cl.
    *A61B 17/08* (2006.01)
(52) U.S. Cl. ....................................... 606/158
(58) Field of Classification Search ............... 600/207, 600/37; 606/157, 158, 201–204, 191, 198, 606/204.15, 204.25, 204.35, 204.45
    See application file for complete search history.

(56) References Cited

U.S. PATENT DOCUMENTS

| | | | | |
|---|---|---|---|---|
| 3,510,923 A | * | 5/1970 | Blake | 606/158 |
| 4,466,437 A | * | 8/1984 | Dyck et al. | 606/201 |
| 5,103,839 A | * | 4/1992 | Shichman | 128/898 |
| 5,304,201 A | * | 4/1994 | Rice | 606/201 |
| 5,591,201 A | * | 1/1997 | Lam | 606/201 |
| 5,727,569 A | * | 3/1998 | Benetti et al. | 128/898 |
| 5,836,311 A | | 11/1998 | Borst et al. | |
| 5,865,730 A | | 2/1999 | Fox et al. | |
| 5,885,271 A | * | 3/1999 | Hamilton et al. | 606/1 |
| 5,894,843 A | | 4/1999 | Benetti et al. | |
| 5,927,284 A | | 7/1999 | Borst et al. | |
| 5,976,069 A | | 11/1999 | Navia et al. | |
| 5,984,864 A | * | 11/1999 | Fox et al. | 600/201 |
| 6,015,378 A | | 1/2000 | Borst et al. | |
| 6,015,427 A | * | 1/2000 | Mueller et al. | 606/232 |
| 6,036,641 A | * | 3/2000 | Taylor et al. | 600/231 |
| 6,050,266 A | * | 4/2000 | Benetti et al. | 128/898 |
| 6,120,436 A | * | 9/2000 | Anderson et al. | 600/201 |
| 6,328,688 B1 | | 12/2001 | Borst et al. | |
| 6,398,726 B1 | * | 6/2002 | Ramans et al. | 600/229 |
| 6,406,424 B1 | * | 6/2002 | Williamson et al. | 600/201 |
| 6,488,618 B1 | * | 12/2002 | Paolitto et al. | 600/37 |
| 2003/0158463 A1 | * | 8/2003 | Julian et al. | 600/104 |

FOREIGN PATENT DOCUMENTS

WO    WO 97/10753    3/1997

* cited by examiner

*Primary Examiner* — Gary Jackson
*Assistant Examiner* — Lindsey Bachman

(57) ABSTRACT

A method for occluding a blood vessel at a compression site is provided. Suction is applied to stabilize a surgical location adjacent the compression site. A first compressor is positioned proximal the surgical location and adjacent the blood vessel. The blood vessel is occluded with the first compressor in response to the positioning. Systems and apparatuses for using the method are also provided.

13 Claims, 5 Drawing Sheets

OCCLUDING AND STABILIZING MEDICAL DEVICE

FIELD OF THE INVENTION

The present invention relates to the field of medical methods and devices for stabilizing and occluding an area of tissue. More particularly, the invention relates to devices that are capable of immobilizing an area of epicardial tissue and of occluding an area of epicardial tissue to permit the heart to be operated on while it is beating.

BACKGROUND OF THE INVENTION

The current leading cause of death in the United States is coronary artery disease in which the coronary arteries are blocked by atherosclerotic plaques or deposits of fat. The typical treatment to relieve a partially or fully blocked coronary artery is coronary artery bypass graft (CABG) surgery.

CABG surgery, also known as "heart bypass" surgery, generally entails using a graft to bypass the coronary obstruction. The procedure is generally lengthy, traumatic and subject to patient risks. Conventional CABG procedures are typically conducted on a stopped heart while the patient is on a cardiopulmonary bypass (CPB) circuit. A stopped heart and a CPB circuit enables a surgeon to work in a bloodless, still operative field. However, there are a number of problems associated with CABG procedures performed while on CPB including the initiation of a systemic inflammatory response due to interactions of blood elements with the artificial material surfaces of the CPB circuit and global myocardial ischemia due to cardioplegic cardiac arrest. For these reasons, avoiding the use of CPB or cardioplegic cardiac arrest may help minimize post-operative complications.

Thus, less invasive methods of cardiac surgery have regained interest. In particular, methods of performing cardiac surgery without stopping the heart (i.e., "beating heart surgery") provide desirable alternatives to the risks of a typical stopped heart CABG procedure. Coronary motion can now be adequately restrained with a mechanical stabilization device. For example, WO97/10753 in the name of Applicant describes such a device. U.S. Pat. Nos. 5,836,311; 5,927,284; 6,015,378; 6,328,688 all assigned to Medtronic, Inc., also describe methods and apparatuses for temporarily immobilizing an area of epicardial tissue.

Beating heart surgical methods, however, still present the challenge of a bloodless field to the surgeon. That is, during beating heart surgery, blood may spill from the wound and obscure visibility. A bleeding artery is difficult to see and, therefore, difficult to perform surgery upon.

In one solution, surgeons practicing beating heart surgery may put a suture or silastic snare around an artery in order to occlude the artery temporarily so that bleeding stops and the artery may be operated upon. Typically, the snare is looped around the artery, using a needle. Circumferential snaring may be used to fold the vessel on one of its sides.

Occluding in such a manner has several disadvantages. Firstly, such an occlusion method requires puncturing the myocardium with the needle in order to loop it around the artery. Secondly, a circumferential snare occludes by folding the artery. This snaring may cause multiple sharp folds, which irritate the intima of the artery and induce a protective layer of protein to be laid down. Therefore, any attempt by the artery to repair intimal damage may activate the mechanism that eventually results in a reoccluded field. Thirdly, the folding that may occur from circumferential snaring may prevent adequate sealing. Multiple radial folds are more difficult to seal and typically require more force to seal than does a single flattening fold.

Thus, a need exists in the medical arts for occluding a vessel, particularly in a beating heart procedure, that overcomes the above.

U.S. Pat. No. 5,976,069 to Navia, et al. discloses an epicardial immobilization frame having one or more expandable members attached to the frame that, upon inflation, temporarily occlude the passage of blood through the vessel or vessels in the operational field defined by the frame.

U.S. Pat. Nos. 6,036,641 to Taylor, et al. and 6,050,266 to Benetti, et al. disclose a compression stabilizer including a pair of substantially planar rectangular contact members attached at one end to a continuous connecting shaft. The contact members are oriented in a substantially parallel fashion such that a target artery is positioned therebetween and passes along the greater length of the contact members when the compression stabilizer engages the heart. The compression stabilizer may include an artery occluder that may be operated to contact the target artery positioned between the contact members to occlude the passage of blood through the target artery.

U.S. Pat. No. 6,120,436 to Anderson, et al. discloses a platform stabilizer having a pair of occluding members configured to slide and move vertically within the platform for positioning over and occluding a section of artery. The platform is sutured to the epicardium of the heart thereby defining an operation field within the platform on the epicardium, and stabilizing the epicardium within the operational field. The occluding members are positioned over and into contact with the epicardium surface over the artery, and temporarily locked in place thereby temporarily occluding a section of artery in the operational field.

All the publications described above are hereby incorporated by reference herein in their respective entireties. As those of ordinary skill in the art will appreciate readily upon reading the Summary of the Invention, the Detailed Description of the Preferred Embodiments and the Claims set forth below, many of the devices and methods disclosed above may be modified advantageously by using the teachings of the present invention.

SUMMARY OF THE INVENTION

One aspect of the present invention provides a method for occluding a blood vessel at a compression site. Suction is applied to stabilize a surgical location adjacent the compression site. A first compressor is positioned proximal the surgical location and adjacent the blood vessel. The blood vessel is occluded with the first compressor in response to the positioning.

The first compressor may also be locked to fix a first compressive force against the blood vessel or the first compressor may be released to release the first compressive force from the blood vessel. The first compressor may be attached to a suction stabilizer to stabilize the surgical location. The first compressor may be ratcheted in order to apply the first compressor to the blood vessel. The surgical location may be further stabilized by applying the first compressor against the surgical location.

A second compressor may also be positioned adjacent the blood vessel, the second compressor located distal the surgical location and the blood vessel may be occluded with the second compressor in response to the positioning. The first and second compressors may be locked to fix compressive forces against the blood vessel or the first and second compressors may be released to release first and second compressive forces from the blood vessel. The first and second compressors may be attached to a suction stabilizer, the suction stabilizer adapted to stabilize the surgical location. The first and second compressors may be ratcheted in order to apply them to the blood vessel. The surgical location may be further stabilized by applying the first and second compressors against the surgical location.

Another aspect of the present invention provides a system for occluding a blood vessel at a compression site. The system includes means for applying a suction to stabilize a surgical location adjacent the compression site, means for positioning a compressor adjacent the blood vessel and proximal the surgical location, as well as means for occluding the blood vessel with the compressor in response to the positioning.

The system may also include means for locking and releasing the compressor in order to fix or release a compressive force against the blood vessel. The system may also include means for attaching the compressor to a stabilizer for stabilizing the surgical location. The system may also include means for ratcheting the compressor to apply the compressor to the blood vessel. The system may also include means for further stabilizing the surgical location by applying the compressor against the surgical location. The system may also include means for positioning a second compressor adjacent the blood vessel and distal the surgical location, as well as means for occluding the blood vessel with the second compressor in response to the positioning.

Yet another aspect of the present invention provides a medical apparatus for performing heart surgery. The apparatus includes a suction stabilizing device, a compressor operably attached to the suction stabilizing device and a positioning member operably attached to the compressor.

The apparatus may also include a support member, at least one suction member and/or at least one screw member, any one of which may be attached to the suction stabilizing device. In one embodiment of the invention, the suction stabilizing device is operably adapted to insert via an endoscopic port. In another embodiment of the invention, the compressor is removably attached to the suction stabilizing device.

The foregoing, and other, features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims in equivalence thereof.

DETAILED DESCRIPTION OF THE PRESENTLY PREFERRED EMBODIMENTS

Figure 1:
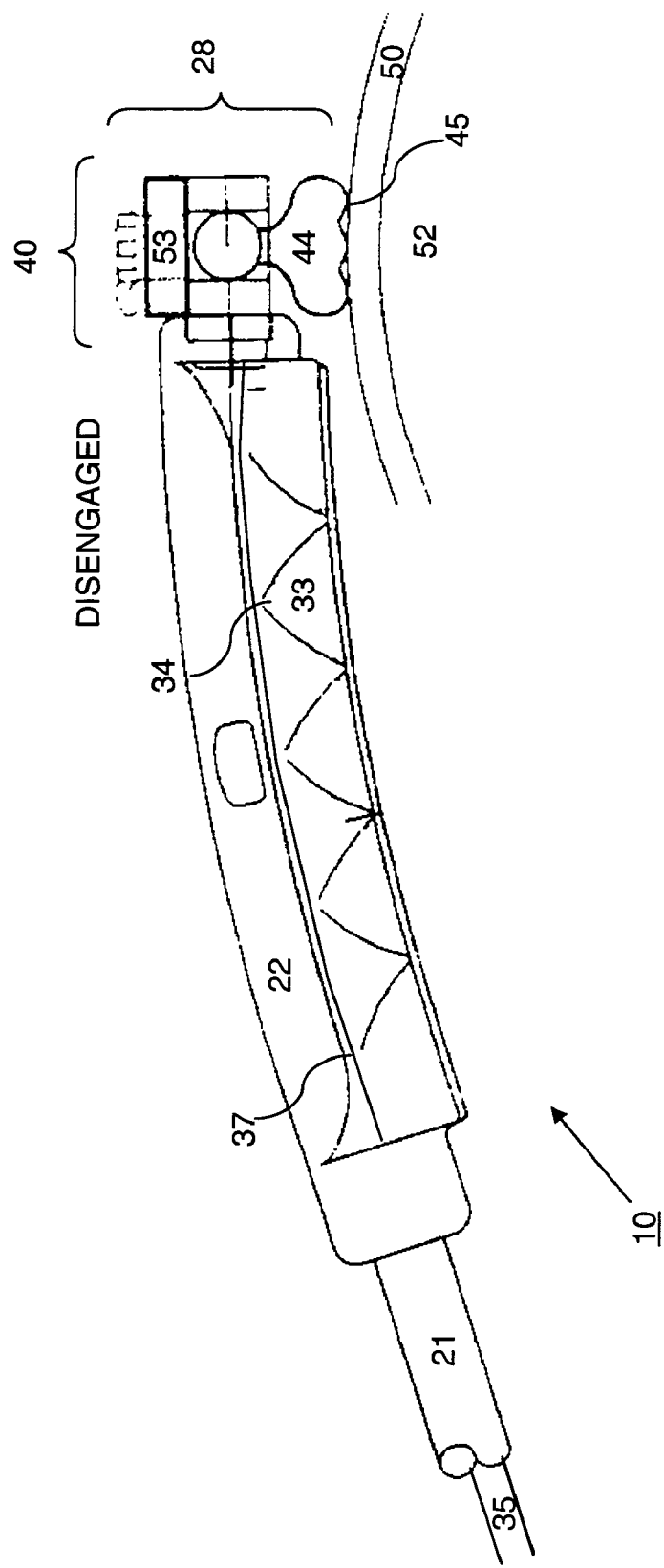
FIG. 1 is a schematic view of one embodiment of a medical occluding and immobilizing device in accordance with the present invention.

FIG. 1 shows a side view of one embodiment of a medical device for occluding and compressing a blood vessel in accordance with the present invention at 10. FIG. 1 shows medical device 10 situated against an artery 50 on a surface of heart 52. The distal end of device 10 comprises at least one paddle 22, and at least one compressor 28. In the embodiment shown in FIG. 1, compressor 28 is attached to the distal end of paddle 22 via a ratchet mechanism 40. As seen in FIG. 1, compressor 28 may further comprise at least one plunger 44, which may or may not include a plurality of protrusions 45. Compressor 28 may also comprise one or more actuating mechanisms 53 separate from or working in conjunction with ratchet mechanism 40. Paddle 22 may further comprise a plurality of suction ports 33. Suction ports 33 may further comprise suction apertures 34. Paddle 22 may further be attached to a suction tube 35 via suction conduit 37. The proximal end of paddle 22 may be connected to a handle 21.

In one embodiment of the invention, when paddle 22 is positioned against the target tissue, a face of paddle 22 adjacent to the surface of the heart 52 may be adapted to conform to the surface of the heart. This may be accomplished by making paddle 22 from a flexible material, such as, for example, a pliable polymer, biocompatible rubber, thermoplastic elastomer or PVC. Alternatively, paddle 22 may be made of a more rigid material covered with an elastic material. The elastic material may cover at least the face adjacent the surface of heart 52. A suction force applied through paddle 22 may cause device 10 to conform more closely to the shape of the target tissue. Paddle 22 may include a malleable stainless steel or other material that is shapeable but not necessarily flexible. Paddle 22 may include a conductive polymer.

In one embodiment of the invention, paddle 22 is a tissue stabilizer such as the tissue stabilizer described in U.S. Pat. Nos. 5,836,311, 5,927,284, 6,015,378, 6,328,688 all assigned to Medtronic, Inc., herein incorporated by reference in their entirety. Paddle 22 may be constructed of any suitable material, such as, for example, a biocompatible material. A biocompatible material would prompt little allergenic response and would be resistant to corrosion when placed within the patient's body. The biocompatible material may additionally be impervious to blood. Furthermore, the biocompatible material would not cause any additional stress to the patient's body. For example, it would not scrape detrimentally against any elements within the surgical site. In one embodiment of the invention, paddle 22 may be constructed of stainless steel or a biocompatible rubber. Alternatively, the biocompatibility of paddle 22 may be enhanced by coating the material of paddle 22 with a biocompatible coating.

Paddle 22 may be colored so that it can be easily visible against the heart. Alternatively, it may be translucent or transparent to provide less obstruction to the surgeon's line of sight.

Figure 2:
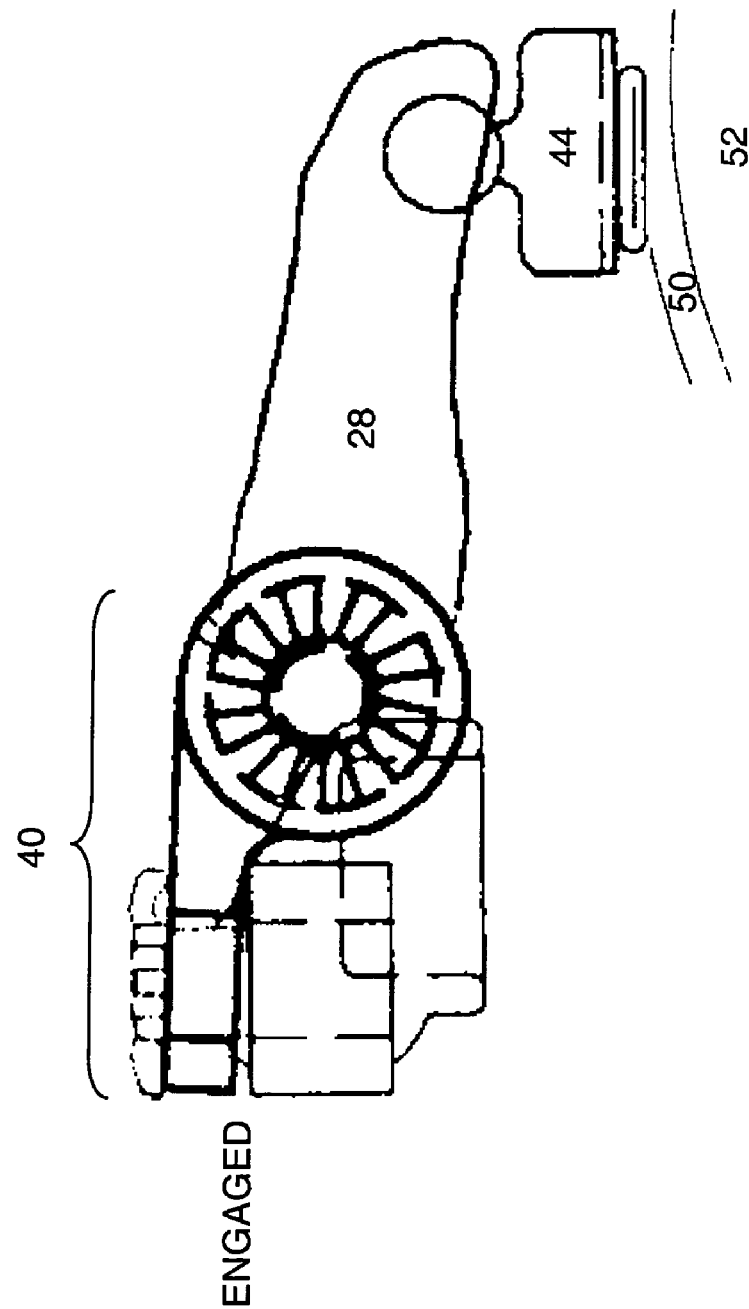
FIG. 2 is another schematic view of the embodiment of the medical occluding and immobilizing device of FIG. 1.
Figure 4:
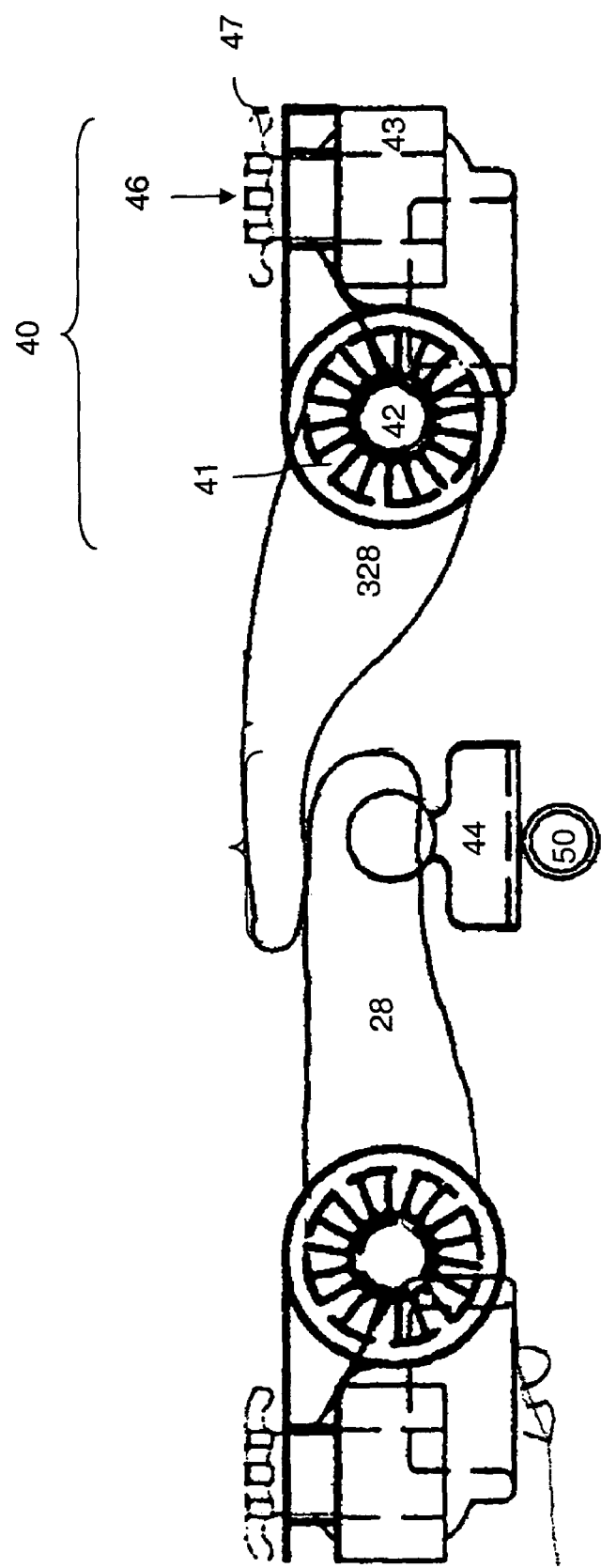
FIG. 4 is another schematic view of the embodiment of the medical occluding and immobilizing device of FIG. 3.

In one embodiment of the invention, compressor 28 may be adapted to apply pressure to the surface of heart 52 and/or to artery 50. Compressor 28 may also be manipulated to apply pressure to a variety of surfaces. Compressor 28 may be in a disengaged position as seen in FIGS. 1 and 4. Alternatively, compressor 28 may be in an engaged position as seen in FIG. 2. In one embodiment of the invention, compressor 28 is an arm able to apply pressure, for example, through plunger 44 to artery 50. Compressor 28 may be constructed of any suitable material such as, for example, a biocompatible material as described above. In one embodiment of the invention, compressor 28 may be constructed of stainless steel, biocompatible plastic or a biocompatible rubber. Compressor 28 may be colored so that it can be easily visible against the heart. Alternatively, it may be translucent or transparent to provide less obstruction to the surgeon's line of sight.

Figure 3:
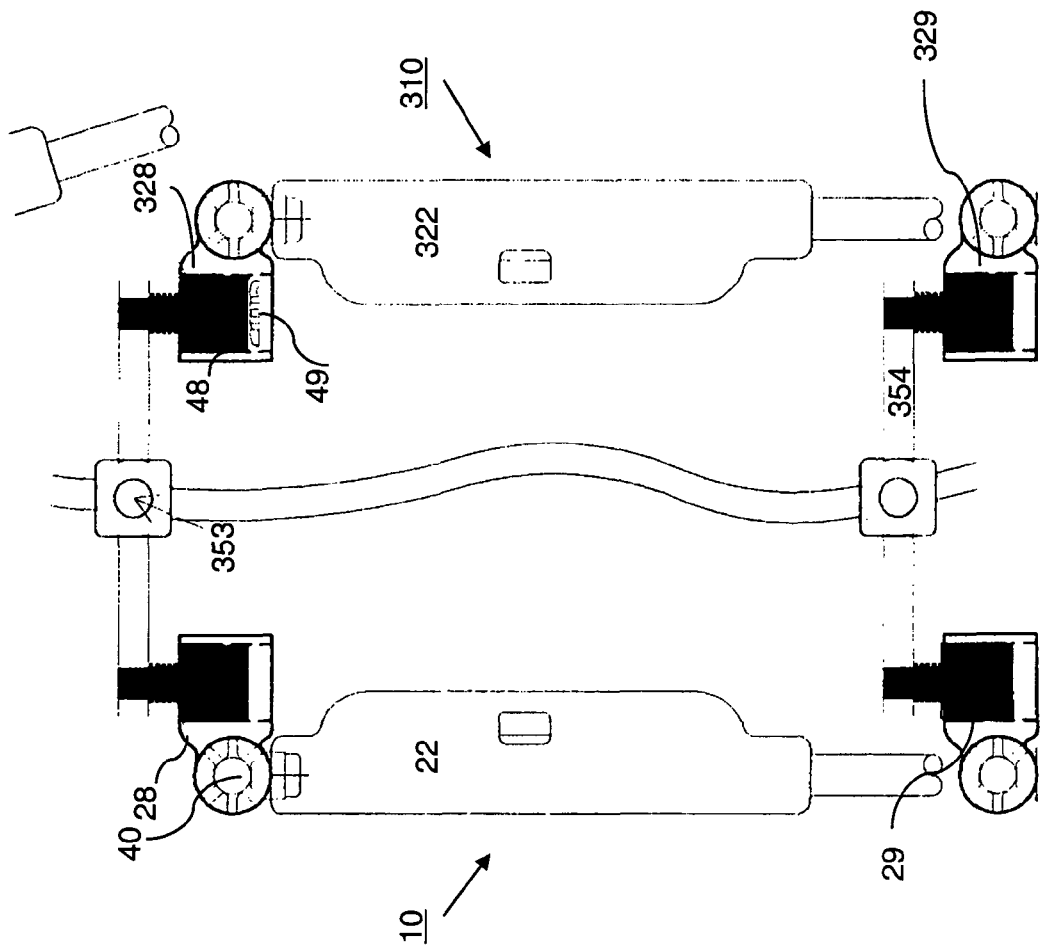
FIG. 3 is a schematic view of another embodiment of a medical occluding and immobilizing device in accordance with the present invention.

In the embodiment shown in FIG. 1, compressor 28 attaches to the distal end of paddle 22. Additional compressors may also be attached to device 10. For example, as seen in FIG. 3, compressor 28 is attached to device 10 at a distal end of paddle 22 while a second compressor 29 is attached to a frame 354 located proximally to paddle 22. In addition, more than one device 10 may be used in accordance with the present invention. This is illustrated in FIG. 3 which shows a second device 310 with a third compressor 328 attached distally to paddle 322 and a fourth compressor 329 attached to a frame 354 located proximally to paddle 322.

Compressors 28, 29, 328, 329 may be attached to devices 10, 310 in any suitable arrangement. For example, as seen in FIG. 1, the compressor 28 may be attached directly to paddle 22. Alternatively, as seen in FIG. 3, one or more of compressors 28, 29, 328, 329 may be attached to a frame 354 surrounding the surgical site. Frame 354 may be made of any suitable material, such as, for example, biocompatible material as described above. Frame 354 may be, for example, a stainless steel tubing arrangement framing the surgical site. Compressors 28, 29, 328, 329 may be attached to frame 354 using any suitable mechanism. In one embodiment of the invention, the compressors are attached to frame 354 using one or more ratchet mechanisms 40 as described further below.

Compressors 28, 29, 328, 329 may be attached to paddles 22, 322 using any suitable mechanism. In one embodiment of the invention, the compressor 28 is attached to paddle 22 using a ratchet mechanism 40. This is illustrated in FIG. 4, which shows a side view of the compressors 28, 328 of FIG. 3.

As seen in FIG. 4, a plug 43 is attached to the end of paddle 22. Plug 43 may be attached to paddle 22 using any suitable means. For example, in one embodiment of the invention, plug 43 is glued into an end of the paddle 22. Plug 43 may be constructed of any suitable material such as biocompatible material described above. In one embodiment of the invention, plug 43 is made of a biocompatible rubber.

Ratchet mechanism 40 may further include a rotor 42. Plug 43 may serve as an anchor around which rotor 42 may rotate. In the embodiment shown in FIG. 4, rotor 42 is restrained by a rotor spring 46. A plurality of fingers 47 on the rotor spring 46 may act to engage the compressor 28 when the compressor is in an engaged or locked position as illustrated in FIG. 2. The fingers 47 may be made of any suitable material such as, for example, biocompatible material as described above. In one embodiment of the invention, the fingers are constructed of plastic. Any suitable number of fingers may be used on the rotor spring 46. For example, in one embodiment of the invention, eight fingers are used per rotor spring 46. Rotor 42 may pivot around the axis provided by plug 43. A cavity within rotor 42 may serve as half of ratchet mechanism 40.

Ratchet mechanism 40 may further include a plurality of teeth 41. These teeth may be positioned radially around a center hub of rotor 42. Ratchet mechanism 40 may further include a gear 48. In one embodiment of the invention, gear 48 further comprises gear teeth 49. Gear teeth 49 may mirror and engage teeth 41. Teeth 41 and corresponding gear teeth 49 may be any suitable shape for engaging each other within ratchet mechanism 42. For example, teeth 41 and gear teeth 49 may be a series of small triangular teeth. Teeth 41, 49 may be constructed of any suitable material such as biocompatible material described above. In one embodiment of the invention, teeth 41, 49 are constructed of biocompatible stainless steel.

Teeth 41, 49 of rotor 42 and gear 48 may be pulled tightly in contact with each other via any suitable mechanism, such as, for example a spring. The spring may be restrained by compressor 28, 29 as seen in FIG. 4.

In one embodiment of the invention, the distal end of the compressor may further comprise a plunger 44. Plunger 44 may be constructed of any suitable material, such as, for example, biocompatible material. In one embodiment of the invention, plunger 44 is constructed of soft, silicone rubber. Plunger 44 may be designed to be atraumatic while still providing maximum occlusion.

As seen in FIG. 1, compressor 28 may further comprise a plurality of protrusions 45. In the embodiment of FIG. 1, three protrusions are shown but any suitable number of protrusions may be used in accordance with the present invention. Protrusions 45 may be molded into the soft silicone body of the plunger 44. Protrusions 45 may serve to provide a tortuous inner path of artery 50 in order to prevent blood leakage. Plunger 44 is designed to press down and flatten vessel 50 in a less traumatic method of occlusion.

Paddle 22 may further comprise a plurality of suction ports 33. The proximal end of paddle 22 may be connected to a handle 21. Paddle 22 may further be attached to a suction tube 35 via suction conduit 37.

Suction tube 35 provides suction to device 10 via suction conduit 37. This conduit 37 communicates suction to the heart's surface via suction port 33 in paddle 22. A source for creating suction is attached to suction tube 35 at one end. The suction source may be, for example, the standard vacuum available in an operating room. The suction source may be coupled to the device 10 with a buffer flask (not shown). Suction may be provided, for example, at a negative pressure of between 200-600 mm Hg or alternatively, at a negative pressure of 400 mm Hg.

As seen in FIG. 1, paddle 22 has a series of suction ports 33 each of which is connected to suction conduit 37 through a suction aperture 34. Suction aperture 34 may be located in the center or at a position slightly off-center of suction port 33. Although the apertures 34 are circular in FIG. 1, other shapes may be used. The suction ports 33 may also be any suitable shape. For example, in the embodiment of FIG. 1, the ports 33 are dome-shaped. Additionally, suction ports 33 may be covered with a covering such as described above to prevent blood or tissue from clogging the openings 34.

The suction ports 33 may be arranged, for example three to six ports in a row, although the specific number of ports and their positions may vary in accordance with the present invention. In one embodiment of the invention, the ports may be arranged linearly and compressor 28 may also be aligned with the ports 33. In one embodiment of the invention, device 10 may be covered with a covering during insertion to prevent blood or tissue from clogging the ports 33, although this is not necessary. Such coverings may include coverings of biocompatible material that would cover device 10. Alternatively, coverings may be placed over ports 33, such as, for example, mesh coverings or ribbed coverings.

Suction apertures 34 may be positioned off center from suction ports 33 so that if a large upwelling of tissue is caused by the suction (which may occur as a blister or bell-shaped curve) the tissue will not immediately close off the suction by obstructing suction aperture 34, as it would if the aperture were in the center of suction port 33. In addition, each suction aperture 34 may have a much smaller diameter as compared to the diameter of suction port 33. This creates a high resistance pathway between suction port 33 and suction conduit 37. Because of this, loss of a tissue-to-port seal in one suction port (and thus loss of fixation of the suction port to the tissue) does not also cause a precipitous pressure drop in the remainder of the suction ports.

In one embodiment of the invention, compressor 28 may be located within one or more of suction ports 33. Alternatively, compressor 28 may replace one or more of suction ports 33.

Figure 5:
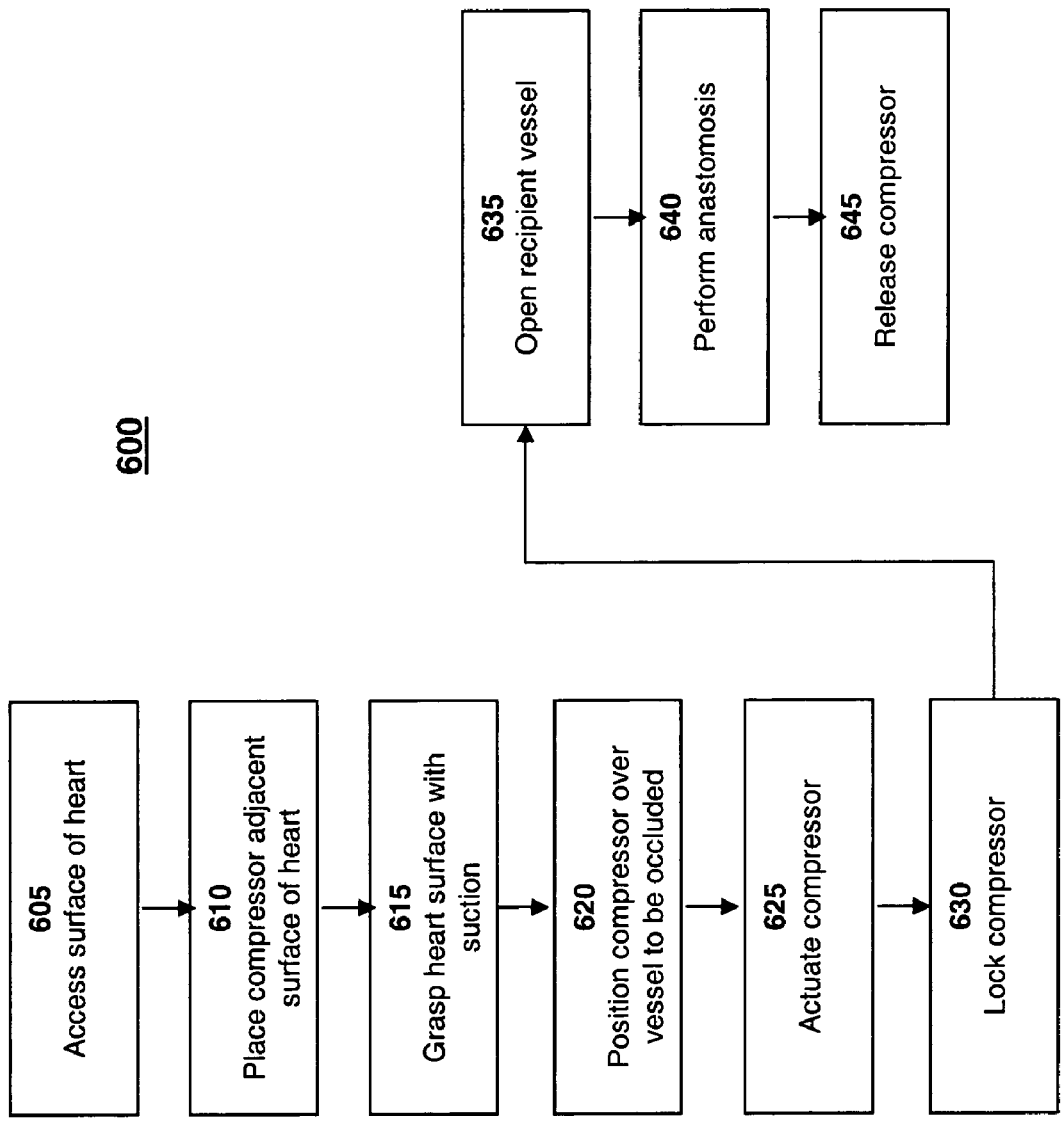
FIG. 5 is a flow diagram of one embodiment of a method for occluding a blood vessel in accordance with the present invention.

FIG. 5 shows one embodiment of a method for occluding a blood vessel in accordance with the present invention at 600.

As seen at block 605, a surgical site, such as the surface of the heart, may be accessed. In one embodiment, surgical access to the local area of heart tissue is achieved through a sternotomy. Alternatively, surgical access to the local area of heart tissue may also be achieved through a mini-thoracotomy, preferably performed within either the fourth or fifth intercostal space. An incision of, for example, approximately 10 centimeters is made into the chest cavity between the ribs. The rib cartilage may be temporarily removed and the ribs surrounding the incision slightly spread apart to provide adequate surgical access to artery 50 and the heart 52.

As seen at block 610, medical device 10 may then be inserted into the chest cavity and placed adjacent a first surface of the heart 52.

As seen at block 615, once the device 10 has been placed adjacent the heart, a suction source may then be used to create suction through the suction tube 35. Via suction conduit 37 through suction ports 33 of the device 10, the suction source may firmly grasp the heart. This suction may be used to lock the device 10 to the myocardium of the heart 52.

As seen at block 620, the compressor may then be positioned over the vessel 50 to be occluded. In order to determine an optimal position for the compressor 28, the surgeon may consider such factors as where the anastomosis will be created, how far upstream from the anastomosis the desired occlusion site should be, whether or not to occlude the vessel downstream from the anastomosis site and whether or not multiple occlusions sites may be desirable.

As seen at block 625, the compressor 28 may be actuated. For example, actuating the compressor 28 may involve rotating the rotor 42 to position the plunger 44 accurately. Then once the plunger 44 is positioned as desired, the compressor 28 may be actuated. For example, the compressor may be pressed down over the plunger 44. This may be accomplished manually by the surgeon using any suitable mechanism. For example, in the embodiment of FIG. 1, the surgeon may press down on actuating mechanism 53. Alternatively, as seen in FIG. 2, compressor 28 may take the form of an arm, which the surgeon may press in order to actuate the compressor. In some embodiments of the invention, the surgeon may actuate more than one compressor separately or concurrently. For example, in the embodiment of FIG. 3, the surgeon may press on actuating mechanism 353 to actuate compressors 28 and 328 simultaneously. Alternatively, as seen in FIG. 4, compressors 28, 328 may take the form of compressor arms. In the embodiment of FIG. 4, the surgeon may press on compressor arm 328, thereby simultaneously actuating compressor 328 and compressor 28.

In some embodiments of the invention, the circular gear teeth 49 and rotor teeth 41 will rotate over one another until sufficient force is exerted to force the spring apart and allow the teeth to ratchet into the next set of teeth. When pushing down on the compressor, the ratchet teeth have a slight incline (15 to 30 degrees) to allow frictional rotation. However, when the teeth engage there may be a 90-degree incline to resist slipping backwards, thereby effectively "locking" compressor 28 in position. To prevent the rotor 42 from turning when the compressor 28 is locked, rotor 42 rotates and locks against finger 47 in the rotor spring 46. This is illustrated in FIG. 2. The engagement of the rotor 42 and the fingers 47 is shown at 53. In addition, the compressor 28 has rotated down, pushing the plunger 44 against artery 50 and compressing artery 50.

Optionally, as seen at block 630, the compressor 28 may be manually locked using any suitable locking mechanism.

Compression of the artery 50 serves to interrupt blood flow in the recipient artery 50. In the embodiment of FIG. 3, compressor 28 is used to interrupt blood flow distally to the anastomotic site while compressor 328 is used to interrupt blood flow proximally to the anastomotic site. Thus device 10 may be used to assist visualization of the anastomosis site by sufficiently occluding artery 50 so that blood flow stops. Additionally, compressor 28 may reduce blood leakage because it applies a single, flat fold compression. This single fold may be more effective than a multiple folded compression.

As seen at block 635, once the blood flow is interrupted, the recipient artery 50 may be opened. This may be accomplished by an arteriotomy as is well known in the art.

As seen at block 640, a surgical procedure, such as an anastomosis, may be performed. For example, the exit (distal end) of the bypass graft may be connected by suturing (or other bonding method, e.g. an anastomotic bonding device) to the recipient artery 50. This is achieved by suturing the inside of the bypass graft to the inside of the recipient artery 50. The rationale of this precise anastomosis suturing is that the inner lining of the vessels (the endothelial layer) is anti-thrombogenic, whereas the outer layer is highly thrombogenic. Thrombosis at the transition of donor to recipient vessel reduces the cross-sectional area of the lumen at the anastomosis and hence jeopardizes the quality of the distal anastomosis. Narrowing (stenosis) of the anastomosis limits the maximum blood flow through the bypass graft.

In a proximal anastomosis, the entrance (proximal end) of the bypass graft needs to be connected to an artery that serves as pressure source of oxygenated blood. If a natural artery can serve as bypass graft, for example, the internal mammary artery in coronary artery bypass grafting, only the distal anastomosis as describe above needs to be made. Sometimes, however, the internal mammary artery is used as free graft or the radial artery is used as arterial conduit and a proximal anastomosis has to be made. Venous bypass grafts always require a proximal anastomosis, because their transformation to an arterial conduit requires connection to a source of arterial blood. Similar to suturing the distal anastomosis of the bypass graft, suturing the proximal anastomosis requires interruption of the source blood flow in the vicinity of the proximal anastomosis site. Again, compressors 28, 29, 328, 329 may be used to achieve interruption of the source blood flow.

In an endoscopic surgical procedure, the device 10 of the present invention is used in a similar manner to that described above. However, surgical access to a local area of heart tissue in an endoscopic procedure is achieved through an endoscopic port in the sternum. This port is a relatively small hole created by a trocar or needle in the sternum. A cannula or tube may be inserted into this hole and the surgical instruments inserted via the cannula. It is contemplated that the device 10 of the present invention may be inserted via a cannula into the surgical space and then placed appropriately on a first surface of the heart and manipulated as described above. It is also contemplated that the device 10 may be attached to the trocar, which creates the hole in the sternum, and thus be inserted in that manner.

Coupling two medical devices 10, 310 in the manner illustrated in FIG. 3 may provide a structure that further improves immobilization of the heart tissue. In one embodiment of the invention, one paddle 22 may be used to stabilize a surgical site, such as an anastomotic site. Alternatively, two paddles 22, 322 may be used to further improve stability of the site.

The frame 354 in accordance with the present invention serves as one means for joining the two stabilizer paddles 22, 322.

Additionally, as seen in FIG. 4, compressing a first compressor 28 on top of a rubber pad on a second compressor 328 may create a friction interface between the two compressors 28, 328. Typically, an interlocking mechanical structure provides more stability than the individual components of the structure. Thus, the interlocking compressors 28, 328 may provide improved stability and thereby improve the anastomosis quality.

As seen at block 645, when compression of the vessel 50 is no longer required, the compressor may be released. This may be accomplished, for example, by releasing the ratchet mechanism 40. For example, the compressor 28 may be pressed against the rotor 42. This serves to compress the spring and disengages the gear teeth 49 from the rotor teeth 41.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

I claim:

1. A method for occluding a blood vessel at a compression site, comprising the steps of:
    applying a suction by way of a tissue stabilizer to stabilize a surgical location adjacent the compression site;
    positioning a first compressor in a first position relative to the tissue stabilizer and adjacent a blood vessel, the first compressor located proximal the surgical location;
    repositioning the first compressor by rotating the first compressor from the first position to a second position in steps as controlled by a series of rotary teeth of a ratchet mechanism so as to apply the first compressor to the blood vessel; and
    occluding the blood vessel with the first compressor in response to the repositioning.

2. The method of claim 1, further comprising the step of: locking the first compressor to fix a first compressive force against the blood vessel.

3. The method of claim 1, further comprising the step of: releasing the first compressor to release a first compressive force from the blood vessel.

4. The method of claim 1, further comprising the step of: attaching the first compressor to a suction stabilizer, the suction stabilizer adapted to stabilize the surgical location.

5. The method of claim 1, further comprising the steps of: positioning a second compressor adjacent the blood vessel, the second compressor located distal the surgical location; and
    occluding the blood vessel with the second compressor in response to the positioning.

6. The method of claim 5, further comprising the step of: locking the first and second compressors to fix a first and second compressive force against the blood vessel.

7. The method of claim 5, further comprising the step of: releasing the first and second compressors to release a first and second compressive force from the blood vessel.

8. The method of claim 5, further comprising the step of: attaching the first and second compressors to a suction stabilizer, the suction stabilizer adapted to stabilize the surgical location.

9. The method of claim 1, wherein the ratchet mechanism comprises a wheel having a surface upon which the rotary teeth are radially positioned around a pivot.

10. A method for occluding a blood vessel at a compression site, comprising the steps of:
    applying a suction by way of a tissue stabilizer to stabilize a surgical location adjacent the compression site;
    positioning a first compressor in a first position relative to the tissue stabilizer and adjacent a blood vessel, the first compressor located proximal the surgical location;
    applying the first compressor to the blood vessel by repositioning the first compressor, wherein the first compressor is repositioned by rotating from the first position to a second position about a pivot of a ratchet mechanism in steps as controlled by a series of rotary teeth of the ratchet mechanism, which series of rotary teeth are radially positioned around the pivot; and
    occluding the blood vessel with the first compressor in response to the applying the first compressor.

11. The method of claim 10, wherein the ratchet mechanism comprises a wheel having a surface upon which the rotary teeth are radially arranged around the pivot.

12. A method for occluding a blood vessel at a compression site, comprising the steps of:
    applying a suction by way of a tissue stabilizer to stabilize a surgical location adjacent the compression site;
    positioning a first compressor in a first position relative to the tissue stabilizer and adjacent a blood vessel, the first compressor located proximal the surgical location;
    positioning a second compressor in a first position relative to the tissue stabilizer and adjacent the blood vessel, the second compressor located distal the surgical location;
    repositioning the first and second compressors by rotating each of the first and second compressors from the first position to a second position in steps as controlled by a series of rotary teeth of a ratchet mechanism of each of the first and second compressors so as to selectively apply the first and second compressors to the blood vessel at proximal and distal surgical positions, respectively;
    occluding the blood vessel with the first compressor in response to the repositioning; and
    occluding the blood vessel with the second compressor in response to the repositioning.

13. The method of claim 12, wherein the ratchet mechanism comprises a wheel having a surface upon which the rotary teeth are radially positioned around a pivot.

* * * * *